United States Patent [19]
Toyoda et al.

[11] Patent Number: 5,836,931
[45] Date of Patent: Nov. 17, 1998

[54] SHORTS TYPE DISPOSABLE DIAPER

[75] Inventors: Harumitsu Toyoda; Kazuhiro Tagawa; Yoshinobu Machida; Kenji Ando; Haruko Kawaguchi, all of Tochigi-ken, Japan

[73] Assignee: Kao Corporation, Tokyo, Japan

[21] Appl. No.: 709,834

[22] Filed: Sep. 10, 1996

Related U.S. Application Data

[63] Continuation of Ser. No. 224,972, Apr. 8, 1994, abandoned.

[30] Foreign Application Priority Data

Apr. 19, 1993 [JP] Japan .................................. 5-091524
Apr. 20, 1993 [JP] Japan .................................. 5-093226

[51] Int. Cl.$^6$ ...................................................... A61F 13/15
[52] U.S. Cl. ........................ 604/385.2; 604/358; 604/378
[58] Field of Search ..................................... 604/358, 372, 604/373, 379, 393, 400, 385.1, 385.2

[56] References Cited

U.S. PATENT DOCUMENTS

| | | | |
|---|---|---|---|
| 4,586,199 | 5/1986 | Birring ........................................... | 2/401 |
| 4,692,163 | 9/1987 | Widlund et al. ...................... | 604/385.2 |
| 4,701,177 | 10/1987 | Ellis et al. ............................ | 604/385.2 |
| 4,813,944 | 3/1989 | Haney et al. ............................ | 604/358 |
| 4,886,697 | 12/1989 | Perdelwitz, Jr. et al. ........... | 604/385.1 |
| 4,897,084 | 1/1990 | Ternstrom et al. ................... | 604/385.2 |
| 4,940,464 | 7/1990 | Van Gompel et al. ................. | 604/396 |
| 5,055,103 | 10/1991 | Nomura et al. ......................... | 604/358 |
| 5,171,239 | 12/1992 | Igaue et al. ............................. | 604/358 |
| 5,188,627 | 2/1993 | Igaue et al. ........................... | 604/385.2 |
| 5,304,159 | 4/1994 | Tanji et al. .............................. | 604/358 |
| 5,382,246 | 1/1995 | Kawano ................................. | 604/385.2 |
| 5,415,649 | 5/1995 | Watanabe et al. . | |

FOREIGN PATENT DOCUMENTS

| | | |
|---|---|---|
| 0320991A2 | 6/1989 | European Pat. Off. . |
| 0454105A1 | 10/1991 | European Pat. Off. . |
| 0483692A1 | 5/1992 | European Pat. Off. . |
| 0487921A3 | 6/1992 | European Pat. Off. . |
| 0529641A1 | 3/1993 | European Pat. Off. . |
| 58-115106 | 7/1983 | Japan . |
| 58-115107 | 7/1983 | Japan . |
| 61-207605 | 9/1986 | Japan . |
| 62-231005 | 10/1987 | Japan . |
| 2-4364 | 9/1990 | Japan . |
| 3-82467 | 4/1991 | Japan . |
| 2242610 | 10/1991 | United Kingdom . |

*Primary Examiner*—John G. Weiss
*Assistant Examiner*—Dennis Ruhl
*Attorney, Agent, or Firm*—Birch, Stewart, Kolasch & Birch, LLP

[57] ABSTRACT

A shorts type disposable diaper includes an absorptive body having a liquid permeable topsheet, a liquid impermeable backsheet, and an absorber interposed between the topsheet and the backsheet. The absorptive body is divided into a stomach side portion, an under-crotch portion, and a back side portion, substantially continuous elastically expansible members being disposed over entire peripheral edge portions of a waist opening and a pair of leg openings which are formed by fixedly connecting confronting opposite side portions between the stomach side portion and the back side portion. The absorber is 8 mm or less in thickness and 100 mm or more in width in the under-crotch portion, and the distance from a side edge of the under-crotch portion of the absorber to the elastically expansible members disposed in the leg opening is 15 mm or more.

16 Claims, 11 Drawing Sheets

SHORTS TYPE DISPOSABLE DIAPER

This application is a continuation of application Ser. No. 08/224,972 filed on Apr. 8, 1994 now abandoned.

BACKGROUND OF THE INVENTION

1. Field of the Invention

This invention relates to a shorts type disposable diaper for the use of infants, incontinent persons and adults, and more particularly to a shorts type disposable diaper which is capable of enhancing fitness and improving leak preventing efficiency.

2. Description of the Prior Art

Conventional disposable diapers are mostly of the flat type, in which a flat diaper body is placed against the wearer and thereafter fastened by a tape fastener located at a side portion (side surface of the waist portion). Recently, there has been developed a so-called shorts type diaper in which side portions thereof are preliminarily fixedly connected without using any tape fastener. Various kinds of shorts type diapers of this type are proposed, including one in which gathers are provided at a waist portion and leg portions, for example. (Japanese Laid Open Patent Application Nos. Sho 58-115106, Sho 58-115107, Sho 62-231005, etc.) These shorts type diapers can all be worn by the wearer in a standing condition as in the case with the normal undergarments. They are intended to be used not only by infants as diapers, but also by month-wise aged babies (babies of about eight to twelve months old) as a toilet training device, or by incontinent persons and adults as a diaper.

The shorts type disposable diaper has the feature, compared with the so-called flat type diaper, in the respect that the wearer can wear it by himself/herself or with the aid of a helper in such a manner as to pull it up and down just like when a normal undergarment is worn. However, there is a demand that such diaper has such functions as a favorable absorption with respect to a bodily liquid, fitness enough to prevent leakage of discharged materials, compliance to various active movements, wearability, easy-to-wear and easy-to-remove characteristics.

In order to fulfill the above demand, Japanese Laid-Open Patent Application No. Hei 2-4364 discloses a construction in which a side panel (side member) is disposed at each side portion for attaching a stomach side portion and a back side portion of a diaper body, and elastically expansible members are disposed respectively at end portions of the stomach side and back side of the diaper body. Japanese Laid-Open Patent Application No. Hei 3-82467 disclosed a construction in which the elastically expansible members around a pair of leg portions comprise first and second members, and central portions of the first and second members are disposed generally at a central portion of an under-crotch portion of the diaper, so that fitness is enhanced at the under-crotch portion to prevent leakage.

However, these disposable diapers have had problems in that the width of the absorber is comparatively small at the under-crotch portion and therefore, leakage often occurs at the area around each leg portion of the wearer.

That is, in the shorts type disposable diaper disclosed in the Japanese Laid-Open Patent Application No. Hei 2-4364, since the side panel is a unitary member, the physical property of elastic expansion of each part is the same and therefore, in order to prevent slip-down and enhance fitness, it is necessary to increase the tightening force. However, this increase of tightening force gives the wearer an undue feel of compression and tends to jeopardize not only the easy-to-wear and easy-to-remove characteristic but also fitness. Moreover, since the side panel is formed as a separate member from the diaper body, the number of component parts is increased, the manufacturing process becomes complicated, and the costs are increased.

In the shorts type disposable diaper of the type as disclosed in the Japanese Laid-Open Patent Application No. Hei 3-82467, the elastically expansible members used around the legs comprise first and second members and the central portions of the first and second members are intersected at generally central portion of the under-crotch portion of the diaper. According to this Laid-Open Application, the employment of such construction enables the elastically expansible members to hold the under-crotch section upwardly to intimately contact the under-crotch section to the wearer's body so that leakage from the under-crotch portion can be prevented. However, actually, this does not work well because the infant wearer's body contour is changed from time to time due to movement, with the result that the diaper slips down and urine leaks from a space formed between the diaper and the wearer's body. The relation between the width dimension of the absorber and the elastically expansible members is not yet improved to the full satisfaction.

Also, since the elastically expansible members provided at the leg openings of the conventional shorts type disposable diaper are usually arranged in the area comparatively near the absorber, they are under the adverse effect of rigidity and bulkiness of the absorber. The result is that the elastically expansible members are not expanded and contracted sufficiently and thus unable to fit to the area around the leg portions of the wearer. As a result, discharged materials leak from the space between the wearer and the diaper, and the diaper slips down due to lack of compliance to the active movements of the wearer.

Furthermore, in the shorts type disposable diaper, the under-crotch portion is formed narrow in order to enhance fitness. In this case, since an absorbing quantity of bodily liquid is decreased, this decrease is supplemented by the anti-leakage function which is obtainable by increasing the elasticity of the elastically expansible members. However, the diaper having such anti-leakage function has the shortcomings in that discharged materials are strongly contacted with the wearer's skin because the diaper intimately contacts the wearer's skin at that area of the under-crotch portion where discharged materials are discharged, thus resulting in soil and rash to the skin.

SUMMARY OF THE INVENTION

It is therefore an object of the present invention to provide a shorts type disposable diaper which is excellent in absorption of bodily liquid, fitness prohibiting leakage of discharged materials, compliance to active movements, wearability, easy-to-wear/easy-to-remove characteristic, and among all, excellent in anti-leakage of discharged materials, this being the weakest point in the conventional shorts type disposable diapers, at the time the diaper is worn by the wearer.

After studying hard about the construction of shorts type disposable diapers, the inventors of the present invention have found that the above object can be achieved by particularly specifying the thickness and width of the absorber and also particularly specifying a positional relation between the absorber and the elastically expansible members located around the leg openings.

The present invention has been accomplished based on the above-mentioned finding. According to the present invention, there is provided a shorts type disposable diaper comprising an absorptive body including a liquid permeable topsheet, a liquid impermeable backsheet, and an absorber interposed between the topsheet and the back-sheet, the absorptive body being divided into a stomach side portion, an under-crotch portion, and a back side portion, substantially continuous elastically expansible members being disposed over entire peripheral edge portions of a waist opening and a pair of leg openings which are formed by fixedly connecting confronting opposite side portions between the stomach side portion and the back side portion, wherein the absorber is 8 mm or less in thickness and 100 mm or more in width in the under-crotch portion, and a distance from a side edge of the under-crotch portion of the absorber to the elastically expansible members disposed in the leg opening is 15 mm or more.

According to the shorts type disposable diaper of the present invention, at the under-crotch portion of the diaper, the absorber is wide or large in width and thin or small in thickness, and moreover, the elastically expansible members are at a location where they are not adversely affected by rigidity of the absorber and act as gathers for the leg openings in an equally effective manner. Accordingly, the diaper of the present invention is capable of effectively preventing leakage of not only urine but also feces, and wearability and easy-to-wear/easy-to-remove characteristic are further enhanced. Moreover, in the case where the side edge areas of the absorber are formed comparatively thin, fitness is even more enhanced and the diaper is hardly displaced even if the infant wearer's body contour is changed due to its active movements.

The shorts type disposable diaper of the present invention is excellent in absorption of bodily liquid, fitness prohibiting leakage of discharged materials, compliance to active movements, wearability, easy-to-wear/easy-to-remove characteristics, and among all, excellent in anti-leakage of discharged materials, this being the weakest point in the conventional shorts type disposable diapers, at the time she diaper is worn by the wearer.

DETAILED DESCRIPTION OF THE INVENTION

Figure 1:
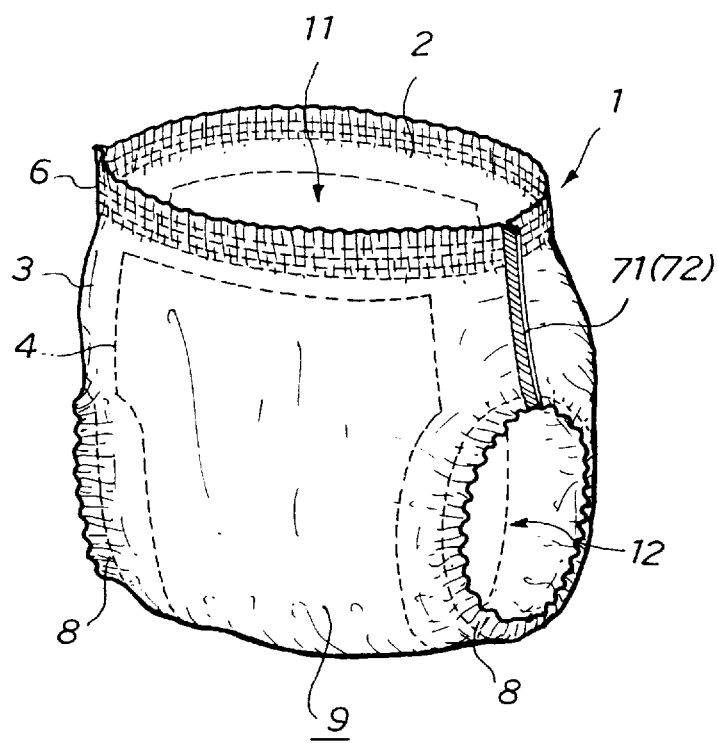
FIG. 1 is a perspective view showing a shorts type disposable diaper according to one embodiment of the present invention.
Figure 2A:
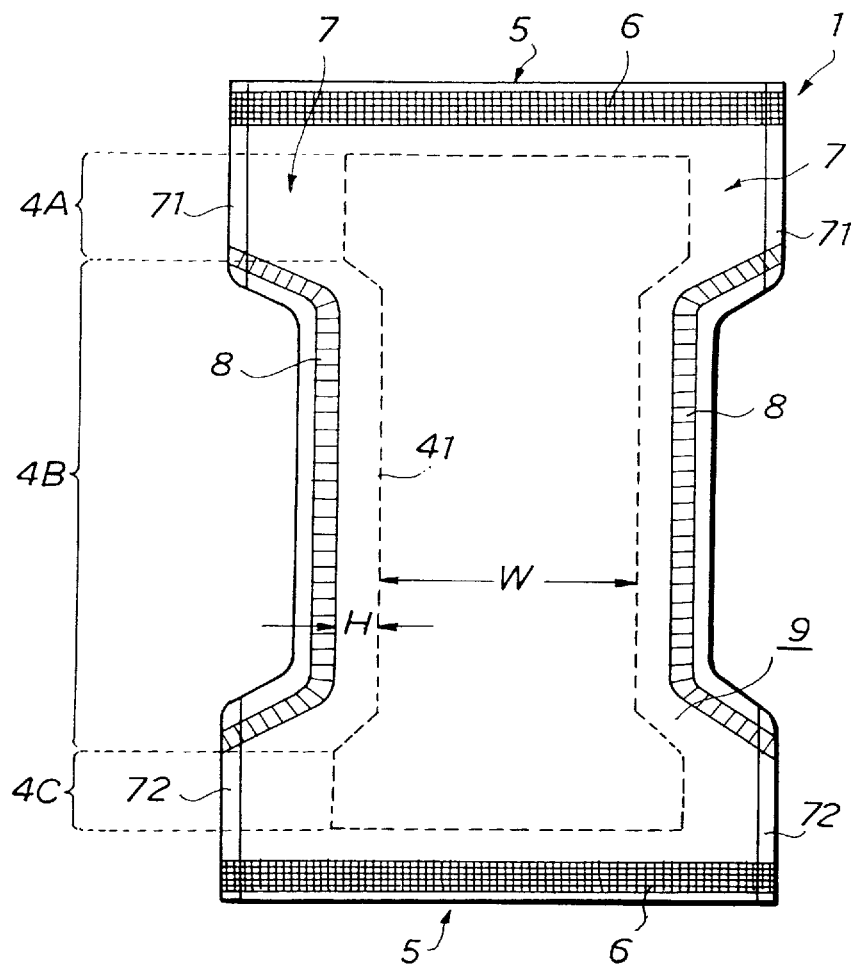
FIGS. 2A and 2B are an inner surface view when the disposable diaper of FIG. 1 is separated at the side waist portions, and a cross-sectional view of the crotch portion, respectively.
Figure 2B:
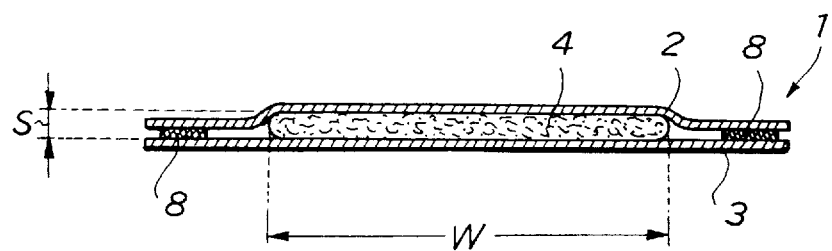

One preferred embodiment of a shorts type disposable diaper of the present invention will be described with reference to the accompanying drawings. In the drawings, FIG. 1 is a perspective view showing a first embodiment of a shorts type disposable diaper of the present invention, and FIGS. 2A and 2B are an inner surface view of the shorts type disposable diaper of FIG. 1 when the disposable diaper is separated at the side waist portions (opposite side portions of the waist area) and a cross-sectional view of the under-crotch portion. FIGS. 3 to 5 are inner surface views of the shorts type disposable diapers according to the second to fourth embodiments when the diapers are separated at the side waist portions and cross-sectional views of the under-crotch portion.

As shown in FIG. 1, a shorts type disposable diaper 1 of this embodiment comprises an absorptive body 9 including a liquid permeable topsheet (inner surface sheet) 2, a liquid impermeable backsheet (rear surface sheet) 3, and an absorber 4 interposed between the topsheet and backsheet. The absorptive body 4 is divided into a front body contact portion (stomach side portion) 4A, an under-crotch portion 4B, and a back contact portion (back side portion) 4C, and substantially continuous elastically expansible members 6, 8 and 8 are disposed over entire peripheral edge portions of a waist opening 11 and a pair of leg openings 12 which are formed by fixedly connecting confronting opposite side portions 71 and 72 between the front body contact portion 4A and the back contact portion 4C. In these respects, the shorts type disposable diaper 1 of this embodiment is just like the conventional shorts type disposable diaper.

In the shorts type disposable diaper 1 of this embodiment, the absorber 4 is 8 mm or less in thickness and 100 mm or more in width in the under-crotch portion 4B, and a distance from a side edge 41 of the under-crotch portion of the absorber 4 to the elastically expansible members 8 disposed in the leg openings is 15 mm or more.

The shorts type disposable diaper 1 of this embodiment will be described in more detail. As shown in FIG. 1, the disposable diaper 1 comprises a liquid permeable topsheet 2 forming that side which contacts the wearer's skin, a liquid impermeable backsheet 3 corresponding to the topsheet 2 and contactable to an undergarment, and an absorber 4 fixedly provided between the topsheet 2 and the backsheet 3 and adapted to absorb discharged materials. The topsheet 2 and the backsheet 3, when in a superimposed condition relative to each other, are further extended in a longitudinal direction of the diaper 1 from the absorber 4 at the front body contact portion 4A and the back contact portion 4C. The extended portions (i.e., waist flaps 5) of the topsheet 2 and backsheet 3 are provided with elastically expansible members 6, respectively. The elastically expansible members 6 form gathers around the waist opening 11. The topsheet 2 and the backsheet 3, when in a superimposed condition relative to each other, are further extended in the width direction of the diaper 1 from the absorber 4 at the front body contact portion 4A and the back contact portion 4C. The extended portions (i.e., the under-crotch portion of the side flaps 7 and 7) are provided with the elastically expansible members 8 and 8, respectively. The elastically expansible members 8 and 8 form gathers around the leg openings 12 and 12, respectively.

As shown in FIG. 2A, in the state where opposite side portions 71 of one side flap 7 of the shorts type disposable diaper 1 are separated from opposite side portions 72 of the other side flap 7, the disposable diaper 1 is formed in a sandglass or hourglass shape in which the under-crotch area of the absorber 4 is twisted. As mentioned above, the topsheet 2 and backsheet 3 are also curvedly formed at the under-crotch area following the shape of the absorber 4. Also as mentioned above, the respective elastically expansible members 8 of each side flap 7 are stretched between the topsheet 2 and the back-sheet 3 such that the expansible members 8 extend respectively along the generally curved peripheral edge portions. The elastically expansible members 8 are contracted in a free condition to form the gathers of FIG. 1, so that the diaper 1 is well fitted to the under-crotch area.

The opposite side portions 71 and 72 are preferably connected such that the feel of the connected portions are soft even after connection. The materials for these portions 71 and 72 are selected such that the connection can be made, for example, by hot-melt type adhesive, or ultrasonic welding means. The length of those portions (opposite side portions 71 and 72) which are to be connected is preferably 2 mm to 100 mm, and more preferably 15 mm to 50 mm.

In this embodiment, as shown in FIG. 2A, the elastically expansible members 8 around the leg opening portions 12 are curved inwardly at the side flaps 9. Moreover, a distance H from the side edge 41 of the absorber 4 in the under-crotch portion 4B is set to be 15 mm or more. The distance H is particularly preferably set to be from 15 mm to 30 mm. The distance H is particularly preferably from 15 mm to 30 mm, and in this embodiment, the distance is 18 mm. If the distance H is less than 15 mm, there is a possibility that the rigidity, etc. of the absorber 4 will adversely affect the gathers and the fitness of the disposable diaper 1 itself becomes bad.

The thickness S of the absorber 4 is preferably 8 mm or less at the under-crotch portion 4B, and particularly 2 to 5 mm. In this embodiment, the thickness S is 5 mm.

If the thickness exceeds 8 mm, rigidity and bulkiness of the absorber 4 are increased in the disposable diaper 1 and fitness a round the wearer's waist portion becomes poor. The width W of the absorber 4 in the under-crotch portion 4B is preferably 100 mm or more, and particularly preferably 120 mm to 160 mm. In this embodiment, the width W is 120 mm. If the width W is less than 100 mm, it becomes difficult for the disposable diaper to sully exhibit its anti-leak property against discharged materials.

Materials used for the topsheet 2, backsheet 3 and absorber 4 are not limited and may be those, known per se, which are already used for conventional disposable diapers and other sanitary goods.

However, with respect to a material of the topsheet 2, a liquid permeable sheet capable of permeating the discharged materials to the absorber 4 and having the feel resembling an undergarment is preferable. An acceptable material of the topsheet 2 may include woven fabric, nonwoven fabric, perforated film, or the like. The peripheral edge of the topsheet 2 is subjected to water repellent treatment by applying a hydrophobic compound such as silicon oil or paraffin wave to the peripheral edge, or by preliminarily applying a hydrophilic compound such as alkylic phosphilic ester to its entirety and then washing the peripheral edge with a hot water. By doing this, leakage of urine, etc. permeating the peripheral edge can be prevented.

The backsheet 3 is preferably a moisture permeable, liquid impermeable sheet which is made by adding a thermoplastic resin with a filler and stretched and which is capable of permeating vapor, and preferably has a feel resembling undergarments. An acceptable liquid impermeable sheet includes a composite material composed of a film and a nonwoven fabric, for example.

The absorber 4 is preferably a high absorption polymer chiefly composed of a comminuted pulp or fibrillated pulp, and also preferably a mixture of a thermoplastic resin, a cellulosic fiber and a high absorption polymer which are subjected to heat treatment. The high absorption polymer may be present in any of the upper layer, intermediate layer and lower layer of the absorber 4, and may also be a mixture with a pulp. The high absorption polymer is preferably in a granular state having a water absorption ability capable of absorbing and holding liquid more than twenty times its dead weight and gelled when it absorbs water. Such a high absorption polymer preferably includes a starch-acrylic acid (salt) graft copolymer, a saponified starch-acrylonitrile copolymer, crosslinked polymer of sodium calboxymethyl-cellulose, acrylic acid (salt) polymer or the like.

The elastically expansible members 6 and 8 used for the disposable diaper 1 preferably include a yarn rubber, a flat rubber, a film type rubber, or a film-like foamed polyurethane, and are also preferably 70 g to 100 g in stress when stretched 150%. The elastically expansible members 8 are preferably formed from a non-woven type material having expansibility and breathability.

Since the shorts type disposable diaper 1 thus constructed is wide or large in width W at the under-crotch portion 4B of the absorber 4 and limited in the thickness S, a wide or large holding space for discharged materials can be formed at the under-crotch portion 4B of the diaper 1 and the absorber 4 is restrained in rigidity and the feel of bulkiness at the under-crotch portion 4B, thereby enhancing wearability and easy-to-wear/easy-to-remove characteristic. Moreover, since the elastically expansible members 8 around the leg openings 12 are located in a position where the rigidity of the absorber 4 is not adversely affected at all, there can effectively be prevented not only urine but also faces from leaking and the diaper is hardly displaced even if the infant wearer's body contour is changed due to active movements of the wearer.

A second embodiment of a shorts type disposable diaper of the present invention will now be described with reference to FIGS. 3A and 3B.

Figure 3A:
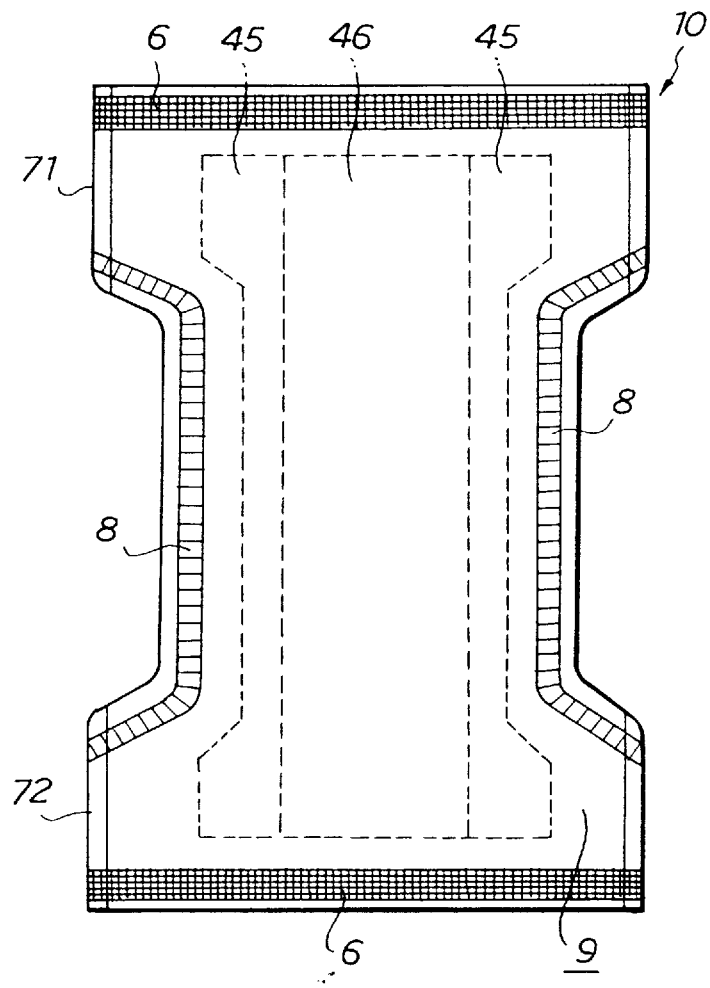
FIGS. 3A and 3B are an inner surface view when a shorts type disposable diaper according to a second embodiment of the present invention is separated at the waist portion and a cross-sectional view of the crotch portion.
Figure 3B:
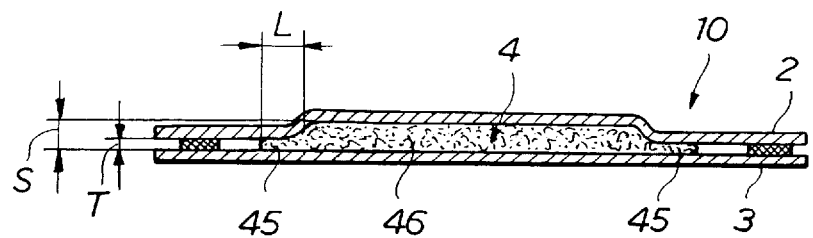

FIG. 3A is an inner surface view of the shorts type disposable diapers according to the second embodiment of the present invention when the diaper is separated at the side waist portions, and FIG. 3B is a cross-sectional view of the under-crotch portion in which the thickness of the absorber is different.

A shorts type disposable diaper 10 of this second embodiment is constructed generally in the same manner as in the first embodiment of FIG. 1, and like parts of the embodiment of FIG. 1 are represented by like reference numerals in FIG. 3 and detailed description thereof is omitted. This second embodiment is different from the first embodiment only in the respect that side edge areas 45 of the absorber 4 are thinner than a central area 46, and these side edge areas 45 are compressed so as to have a thin thickness. The width L of the thin side edge areas 45 is preferably 5 mm to 30 mm and particularly preferably 10 mm to 20 mm. The width T of the thin side edge area 45 is preferably ⅟₁₀ to ½ of the thickness S (same to the thickness S of the first embodiment) of the central area 46 and particularly preferably 1 mm to 3 mm.

Also in the shorts type disposable diaper 10 thus constructed, there can be exhibited the same functions as in the first embodiment of FIG. 1. In addition, there is almost no adverse effect from rigidity, etc. of the absorber 4, and wearability and fitness are further enhanced.

Figure 4A:
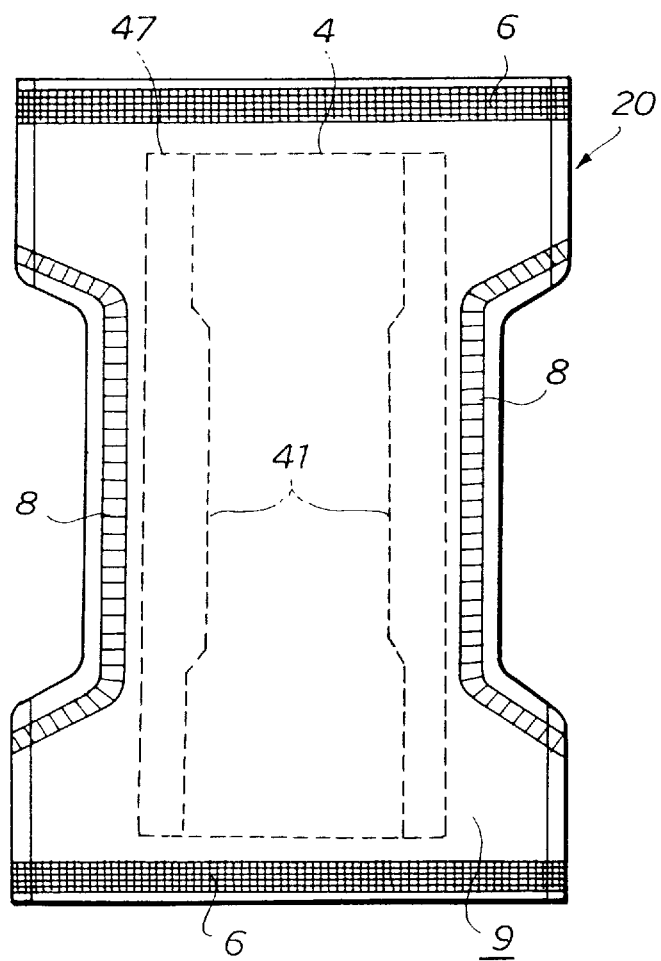
FIGS. 4A and 4B are an inner surface view when a shorts type disposable diaper according to a third embodiment of the present invention is separated at the waist portion and a cross-sectional view of the crotch portion.
Figure 4B:
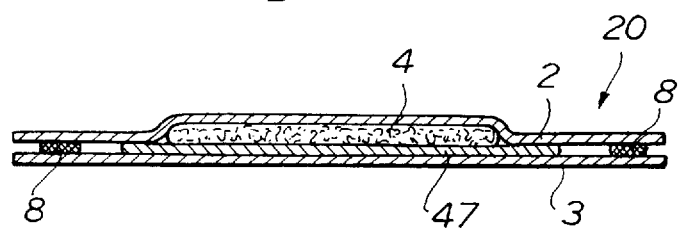

FIG. 4A is an inner surface view of the shorts type disposable diapers according to the third embodiment of the present invention when the diaper is separated at the side waist portions, and FIG. 4B is a cross-sectional view of the under-crotch portion.

A short s type disposable diaper 20 of this third embodiment is constructed generally in the same manner as in the first embodiment of FIG. 1, and like parts of the embodiment of FIG. 1 are represented by like reference numerals in FIG. 4 and de tailed description thereof is omitted. This third embodiment is different from the first embodiment only in the respect that an absorptive paper 47 is provided between the absorber 4 and the back-sheet 3 and the absorptive paper 47 forms the side edge areas. That is, the absorber 4 does not have the side edge areas 45 of FIG. 3, and the absorptive paper 47, this being wider than the absorber 4, is extended outwardly, preferably 5 mm to 30 mm and more preferably 10 mm to 20 mm, thereby forming the side edge areas. The thickness of that portion where the absorber 4 and the absorptive paper 47 are overlapped with each other is the same to the thickness S which is described with reference to the first embodiment, and the thickness of the absorptive paper 47 is the same to the thickness T of the side edge area which is described with reference to the second embodiment. Material used for the absorptive paper 47 is not limited and may be those which are conventionally used for sanitary goods such as disposable diapers. For example, it is preferable to use, in accordance with necessity, a natural pulp, a synthetic fiber, or the like, and particularly preferably a bulky cellulosic fiber, or the like.

Also in the shorts type disposable diaper 20 thus constructed, there can be exhibited the same functions as in the second embodiment of FIG. 3. In addition, the absorptive paper 47 undertakes a part of the role of the absorber 4 and therefore, the disposable diaper 20 is further enhanced in fitness.

Figure 5A:
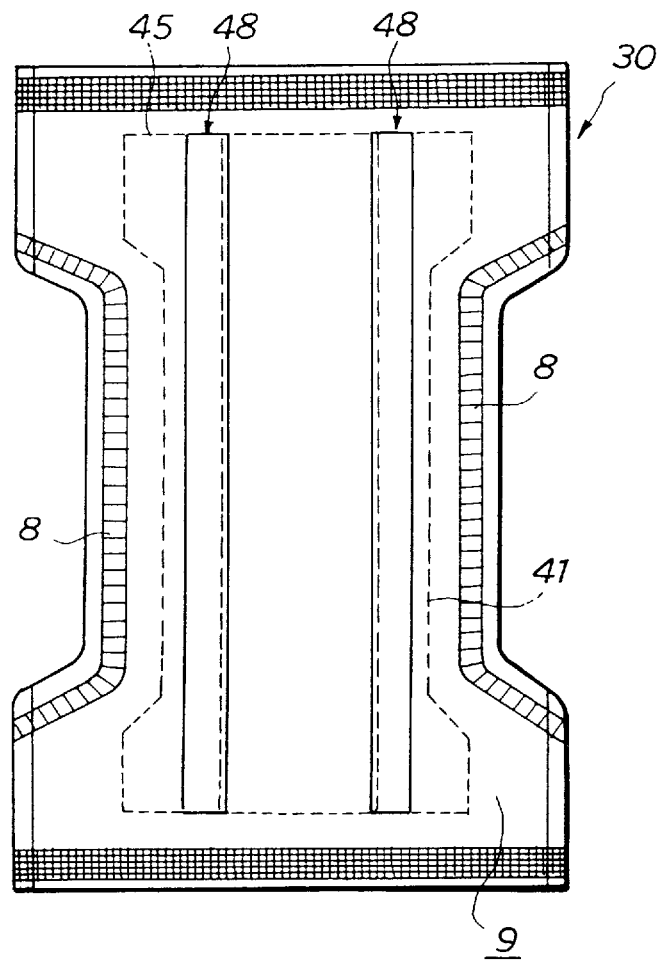
FIG. 5A and 5B are an inner surface view when a shorts type disposable diaper according to fourth embodiment of the present invention is separated at the waist portion and a cross-sectional view of the crotch portion.
Figure 5B:
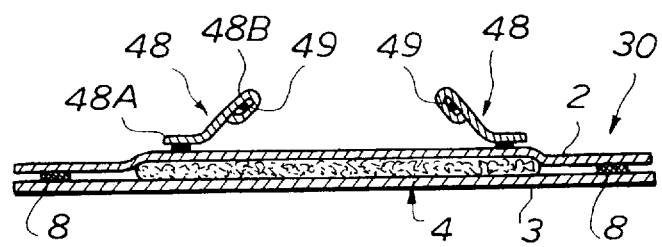

FIG. 5A is an inner surface view of the shorts type disposable diapers according to the fourth embodiment of the present invention when the diaper is separated at the side waist portions, and FIG. 5B is a cross-sectional view of the under-crotch portion.

A shorts type disposable diaper 30 of this fourth embodiment is constructed generally in the same manner as in the first embodiment of FIG. 1, and like parts of the embodiment of FIG. 1 are represented by like reference numerals in FIG. 5 and detailed description thereof is omitted. This fourth embodiment is different from the first embodiment of FIG. 1 only in the respect that three-dimensional gathers 48 and 48, which have fixed points at the side edge areas 45 of the absorber 4, respectively, are provided. That is, the three-dimensional gathers 48 are provided on the upper surface of the topsheet 2 located on the side edge areas 45 which are located by a width of about 5 mm to 20 mm inwardly from the side edges 41 of the absorber 4. The three-dimensional gathers 48 having a belt-like configuration are fixed at one side peripheral edge 48A thereof to the upper surface of the topsheet 2. The other side peripheral edge 48B of the three-dimensional gathers 48 is defined as a free end on which the elastically expansible member 49 is mounted.

Also in the shorts type disposable diaper 30 thus constructed, there can be exhibited the same functions as in the first embodiment of FIG. 1. In addition, bodily liquids such as urine are not partly leaked from the surface of absorber 4, and leakage of solid discharged materials can also be positively prevented, thereby further enhancing the anti-leak property of the shorts type disposable diaper 30. The diaper having the three-dimensional gathers 48 according to the fourth embodiment is more preferably used in combination with the absorber of FIG. 3 or 4 in which the side edge areas are thin.

Next, a shorts type disposable diaper according to a fifth embodiment of the present invention will be described with reference to the drawings.

Figure 6:
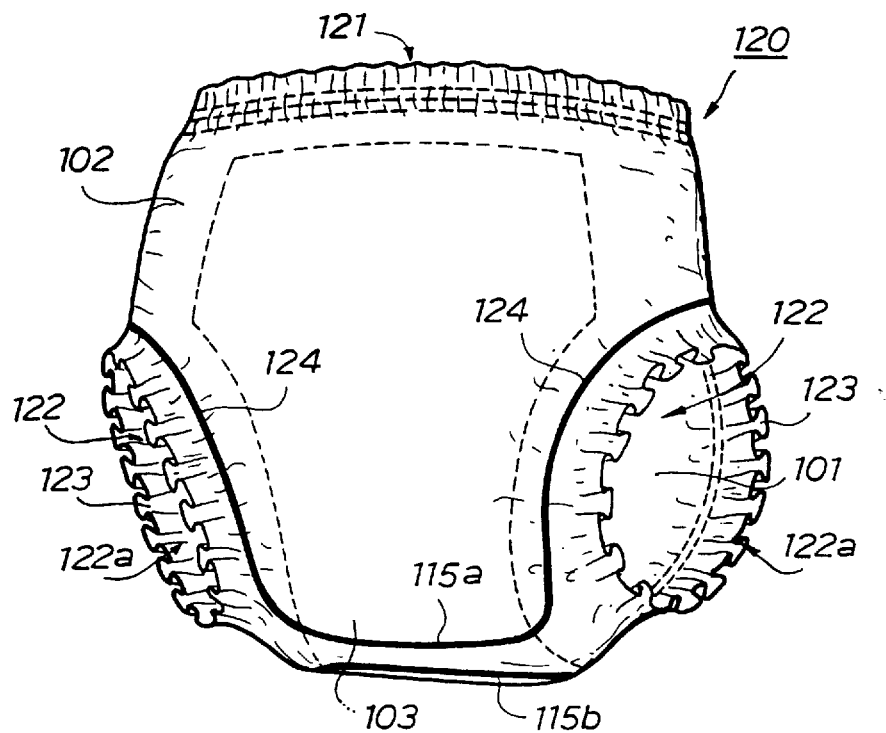
FIG. 6 is a perspective view showing a shorts type disposable diaper according to a fifth embodiment of the present invention.
Figure 7:
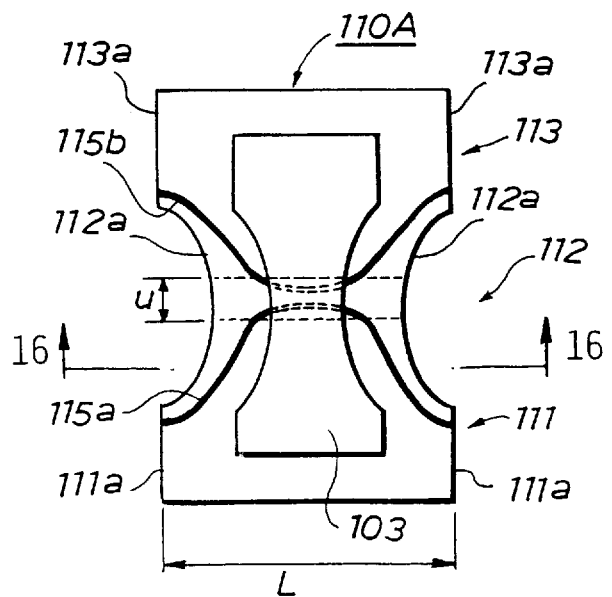
FIG. 7 is a plan view, partly omitted, showing an absorptive body forming the shorts type disposable diaper of FIG. 6.

FIG. 6 is a perspective view showing a fifth embodiment of a shorts type disposable diaper of the present invention, and FIG. 7 is a plan view, partly omitted, of an absorptive body which is in a developed condition.

As shown in FIG. 6, the disposable diaper 120 of this fifth embodiment comprises an absorptive body 110A including a liquid permeable topsheet 101 forming that side which contacts the wearer's skin, a liquid impermeable backsheet 102 corresponding to the topsheet 101, and an absorber 103 provided between the topsheet 101 and the backsheet 102 and adapted to absorb discharged materials. The absorptive body 110A comprises a stomach side portion 111, an under-crotch portion 112, and a back side portion 113. Opposite side edge portions 111a and 111a, and 113a and 113a of the stomach side portion 111 and back side portion 113 respectively are fixedly connected to form a waist opening 121 and a pair of leg openings 122 and 122. This construction is the same as the conventional diaper.

As shown in FIG. 7, the absorptive body 110A used for the shorts type disposable diaper of this fifth embodiment is curvedly twisted at the central portion (under-crotch portion 112) in a developed condition (condition before connection). The absorptive body 110A comprises first and second elastically expansible members 115a and 115b which are fixedly stretched respectively on the side of the stomach side portion and on the side of the back side portion such that the expansible members extend respectively, at the stomach side portion and back side portion, along an inner side of a part of one side edge portion and an inner side of one side edge portion 112a of the under-crotch portion 112, then across the center of the under-crotch portion and along an inner side of the other side edge portions 112a, 111a and 113a. The first and second elastically expansible members 115a and 115b are in parallel proximal relation to each other at the center of the under-crotch portion 112.

Figure 15:
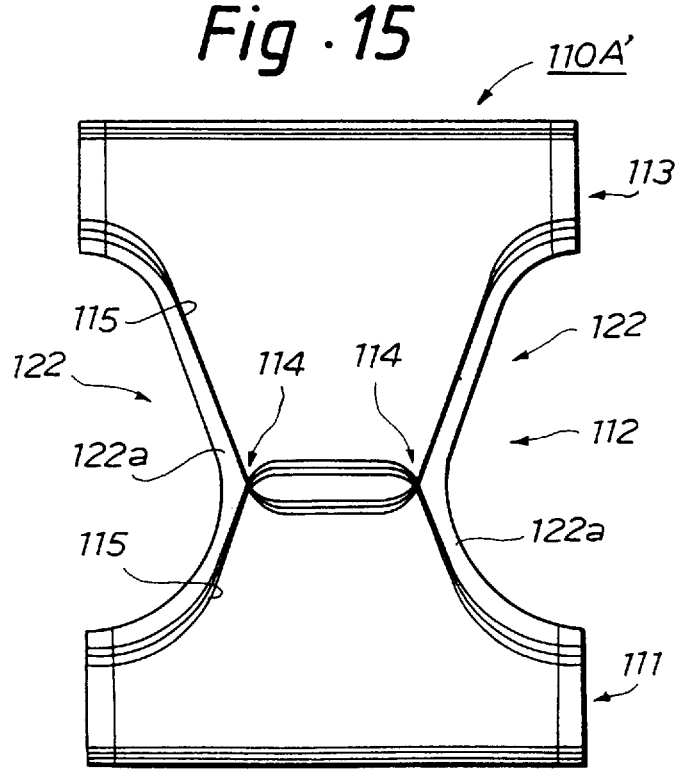
FIG. 15 is a view, like FIG. 10 (absorber is omitted), showing one example of an absorptive body forming a conventional shorts type disposable diaper.

The absorptive body 110A will be described in more detail. A distance between the first and second elastically expansible members 115a and 115b at the under-crotch portion 112 is just enough to prevent leakage of discharged materials. The respective outermost elastically expansible members are located preferably in a range from 0 mm to 20 mm. If it is smaller than 0 mm, there is formed an area surrounded by the elastically expansible members as shown in FIG. 15. This is not desirable in view of appearance. In addition, a contracting force of the elastically expansible members is disturbed at the area of intersection and leakage tends to occur at that portion. In contrast, if it exceeds 20 mm, there occurs an area where no elastically expansible member is provided around the peripheral edge portion of each leg opening and therefore, leakage likewise tends to occur at that portion.

The width and thickness of the absorber 113 at the under-crotch portion 112 are the same as in the first embodiment. The distances from the side edges of the absorber 103 to the elastically expansible members 115a and 115b provided around the leg openings 122 are shorter by the dimensions of those portions of the respective elastically expansible members 115a and 115b crossing the center of the under-crotch portion, i.e., the portion of the width u 0–20 mm in the longitudinal direction of the diaper at the center of the under-crotch portion 112.

The elastically expansible members are not necessarily fixed at the under-crotch portion 112. It is rather preferable in view of appearance that the elastically expansible members are left unfixed. Moreover, if the elastically expansible members are left unfixed in this way, the expanding stress of the elastically expansible members is not disturbed.

Figure 9:
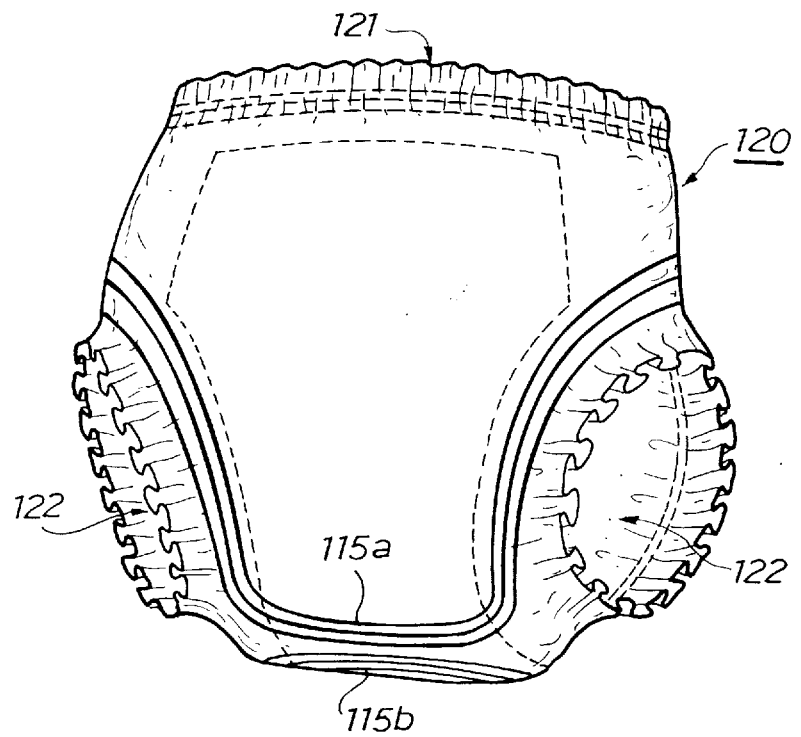
FIG. 9 is a perspective view showing a shorts type disposable diaper according to a sixth embodiment of the present invention.

The first and second elastically expansible members 115a and 115b are not necessarily single in number. As shown in FIG. 9, a plurality of thread-like expansible members may be arranged at spaces. Also, the elastically expansible members may be arranged such that the expanding stresses of the first and second elastically expansible members 115a and 115b are different from each other. In the case where a plurality of elastically expansible members are arranged, the distance between the respective members is preferably in a range from 0.5 mm to 5 mm.

As shown in FIG. 6, the shorts type disposable diaper 120 of this embodiment is constructed such that the absorptive body 110A is fixedly connected at the opposite side edge portions 111a and 111a of the stomach side portion and at the opposite side edge portions 113a and 113a of the back side portion 113 so that elastic annular portions 124 and 124 are formed by the elastically expansible members 115a and 115b, respectively. In this way, gathers 123 and 123 are formed around the peripheral edge portions 122a and 122a of the pair of leg openings 122 and 122, respectively. In FIG. 6, the respective elastically expansible members 115a and 115b are shown by solid lines instead of broken lines for the sake of convenience.

Since the shorts type disposable diaper of this embodiment is constructed in the manner mentioned above, the effect of anti-leakage is high and the wearing feel is excellent.

Figure 8:
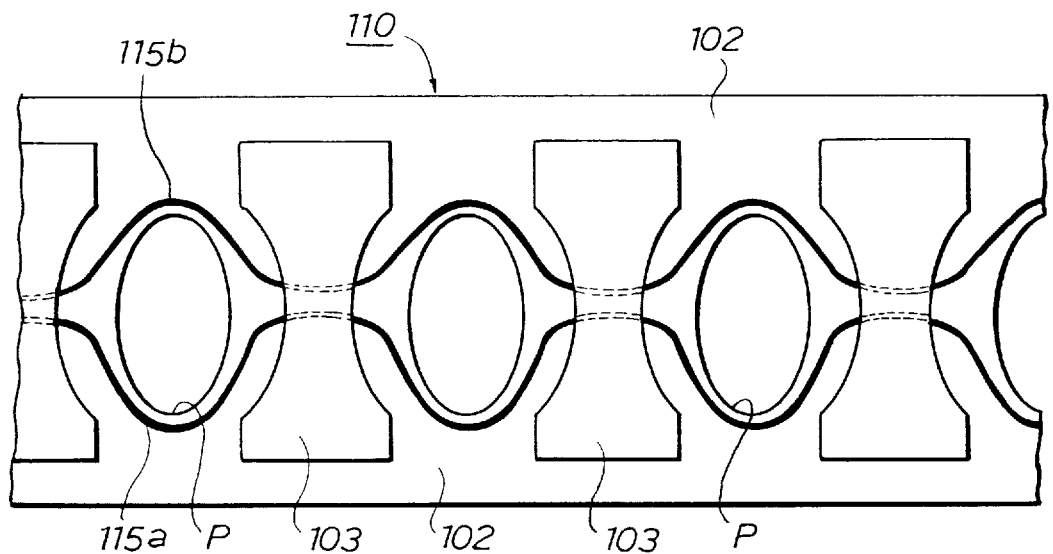
FIG. 8 is a plan view showing an absorptive body continuous member used for manufacturing the shorts type disposable diaper of FIG. 6.
Figure 10:
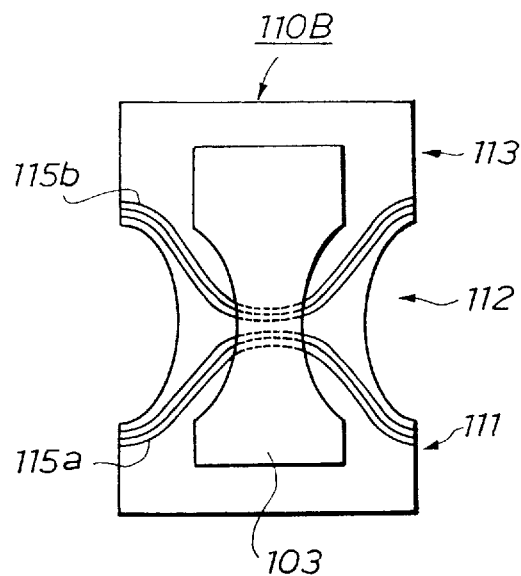
FIG. 10 is a view, like FIG. 7, showing an absorptive body forming the shorts type disposable diaper according to the sixth embodiment of the present invention.
Figure 11:
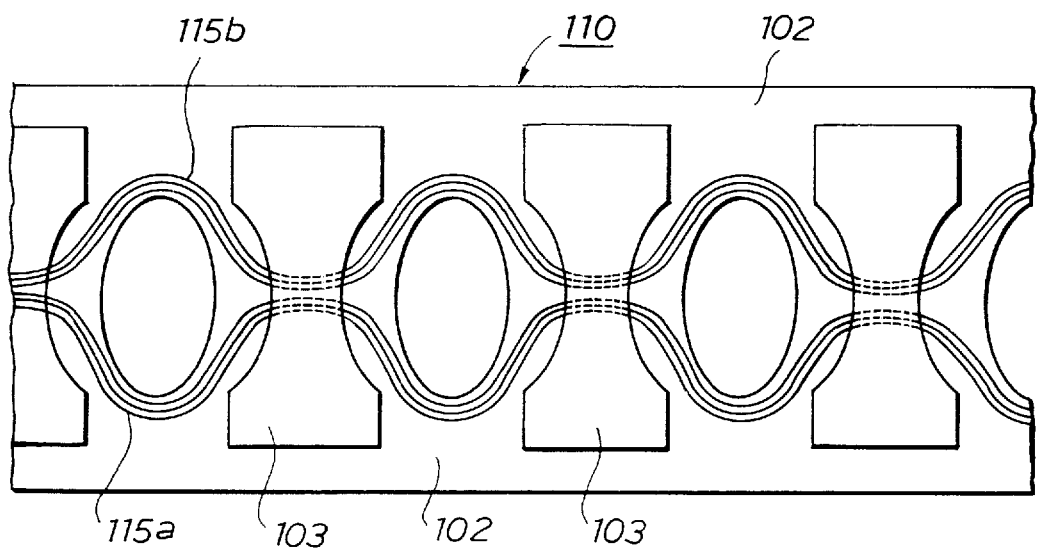
FIG. 11 is a plan view showing an absorptive body continuous member used for manufacturing the shorts type disposable diaper according to the sixth embodiment of the present invention.

With reference to the absorptive body constituting the shorts type disposable diaper of the present invention, there may be used, aside from the absorptive body 110A of FIG. 7, an absorptive body 110B (see FIG. 10) obtained by cutting an absorptive body continuous member 110 of FIG. 11 as in the case where the absorptive body 110A is obtained from the absorptive body continuous member 110 of FIG. 8, that is, an absorptive body 110B is obtained by such that the first and second elastically expansible members 115a and 115b comprise a plurality of members and they are stretched in parallel relation at the under-crotch portion 112. In this case, there can be obtained the shorts type disposable diaper according to a sixth embodiment of FIG. 9. The disposable diaper of FIG. 9 also has substantially the same construction and effect as the shorts type disposable diaper 120 of FIG. 6 and is capable of providing a favorable wearing condition about the waist portion.

Figure 12:
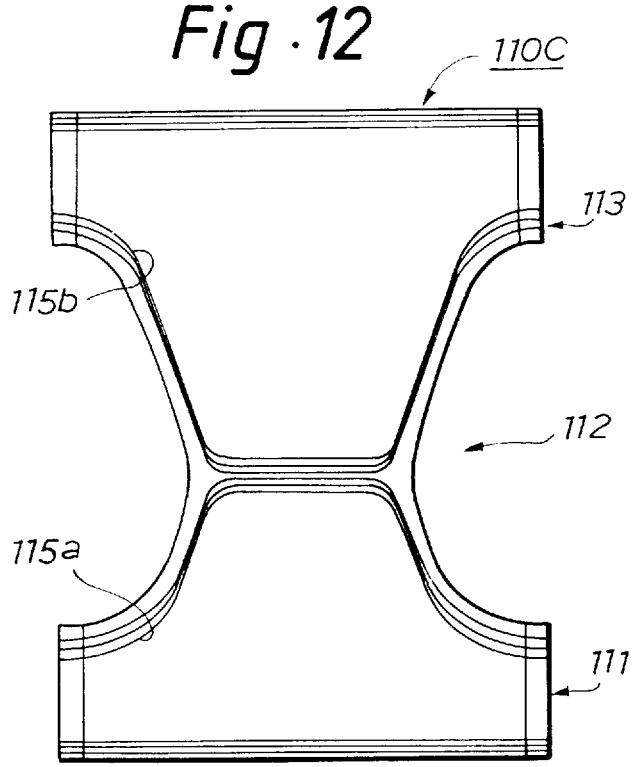
FIG. 12 is a view, like FIG. 10 (absorber is omitted), showing another example of an absorptive body forming the shorts type disposable diaper of the present invention.
Figure 13:
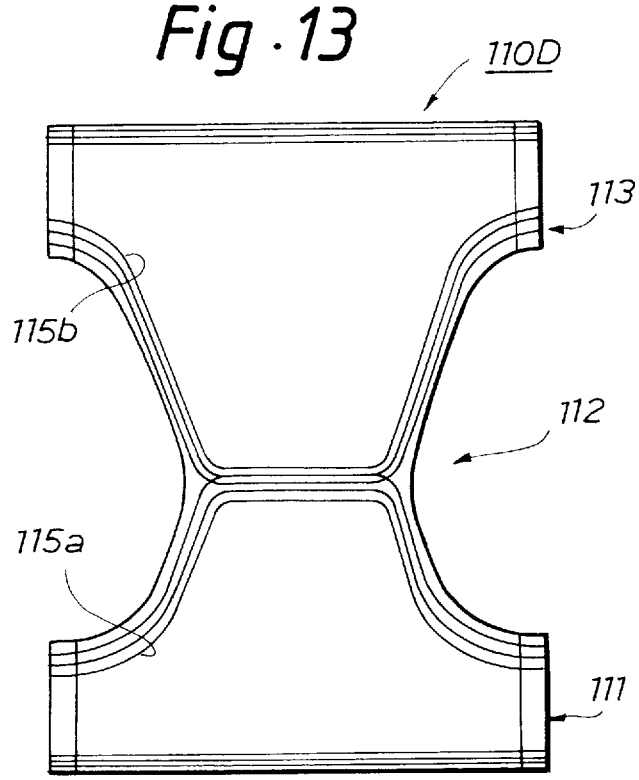
FIG. 13 is a view, like FIG. 10 (absorber is omitted), showing a further example of an absorptive body forming the shorts type disposable diaper of the present invention.
Figure 14:
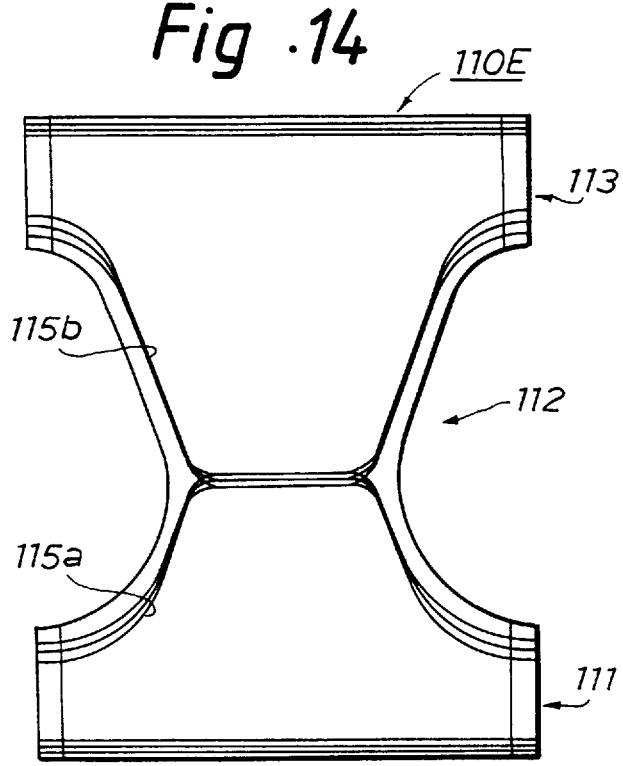
FIG. 14 is a view, like FIG. 10 (absorber is omitted), showing a still further example of an absorptive body forming the shorts type disposable diaper of the present invention.

Other absorptive bodies 110C, 110D and 110E obtained respectively by cutting other absorptive body continuous bodies (not shown) in the same manner as described above may be used as the absorptive body constituting the shorts type disposable diaper of the present invention. As shown in FIGS. 12, 13 and 14 respectively, in these absorptive bodies 110C, 110D and 110E, the first and second elastically expansible members 115a and 115b comprise a plurality of members respectively, and the overlapping degree of the first and second elastically expansible members is changed while maintaining the mutual parallel arrangement condition at the under-crotch portion 12. The absorptive body 110C has the two elastically expansible members in contact with each other, the absorptive body 110D has the two elastically expansible members partly overlapped, and the absorptive body 110E has the two elastically expansible members fully overlapped. In the case where these absorptive bodies 110C, 110D and 110E are used, there can be obtained shorts type disposable diapers having substantially the same construction and effect as the shorts type disposable diaper 120 of FIG. 6, and which is capable of providing a favorable wearing condition about the waist portion.

One mode for carrying out the method of manufacturing the shorts type disposable diaper 120 according to the fifth embodiment will now be described with reference to FIGS. 6 to 8.

Here, FIG. 8 is a plan view of a continuous member of the absorptive bodies used for manufacturing the product of the present invention shown in FIG. 6.

In order to manufacture the shorts type disposable diaper of FIG. 6, first, as shown in FIG. 8, the first and second elastically expansible members 115a and 115b are fixedly stretched on the continuous liquid impermeable backsheet 102 having a predetermined width dimension (corresponding to the longitudinal length of the shorts type disposable diaper in its developed condition) at a space equal to the width L of the absorptive body 110A of FIG. 7 in such a manner as to sway in the width direction of the backsheet 102 but in opposite directions and in proximal parallel relation at the longitudinal center (the undercrotch portion 112) of the absorber 103, which is later provided, on the side of the backsheet 102. Then, the absorber 103 is arranged such that the proximal portions of the elastically expansible members 115a and 115b are located at a widthwise central portion of the absorber 103 and at an outer surface side of the under-crotch portion 112. Thereafter, the continuous liquid permeable topsheet (not shown) of a predetermined width dimension is arranged on the absorber 103. By this, an absorptive body continuous member 110 of the type shown in FIG. 8 is manufactured.

Subsequently, the absorptive body continuous member 110 obtained in the above-mentioned manufacturing process is cut at central portions between the adjacent absorbers 103 and 103. By this, a plurality of absorptive bodies 110A of the configuration as shown in FIG. 7 are obtained. In this cutting process, the topsheet 101 and backsheet 102 are cut away at the circular portion P of FIG. 8 simultaneously with the cutting operation, or slightly earlier or later than the cutting operation, or after the connection between the opposite side edge portions, such that the opposite side edge portions of the under-crotch portion 112 are curvedly twisted as shown in FIG. 7. Thereafter, the respective absorptive bodies 110A obtained in the above-mentioned manufacturing process are connected at the opposite side edge portions 111a and 111a of the stomach side portion 111 and at the opposite side edge portions 113a and 113a of the back side portion 113. As a result, there can be obtained a shorts type disposable diaper 120 of the type as shown in FIG. 6.

It is also possible to obtain the absorptive body 110A of FIG. 7 in such a manner as that after the respective absorptive bodies 110A are connected at the opposite side edge portions 111a and 111a of the stomach side portion 111 and at the opposite side edge portions 113a and 113a of the back side portion 113, it is cut away at the central portions between the adjacent absorptive bodies 103 and 103.

Also, there can be obtained the absorptive body continuous member 110 of FIG. 11 and the absorptive body 110B of FIG. 10 obtainable by cutting the absorptive body continuous body 110 in such a manner as that the elastically expansible members 115a and 115b respectively comprise three members.

Furthermore, by partly changing the swaying pattern of the elastically expansible members 115a and 115b in the above mode, there can be obtained the absorptive bodies 110C, 110D and 110E of FIGS. 12 to 14.

Also in the case where the absorptive bodies 110B to 110E are used, there can be obtained a shorts type disposable diaper of the type as shown in FIG. 6 in the same manner as in the case where the absorptive body 110A is used.

According to the above-mentioned manufacturing method, an absorptive body continuous member can be manufactured easily and successively because at least two elastically expansible members are fixedly stretched in predetermined position at predetermined spaces and in a swaying manner or pattern in the width direction of the continuous backsheet.

Figure 16:
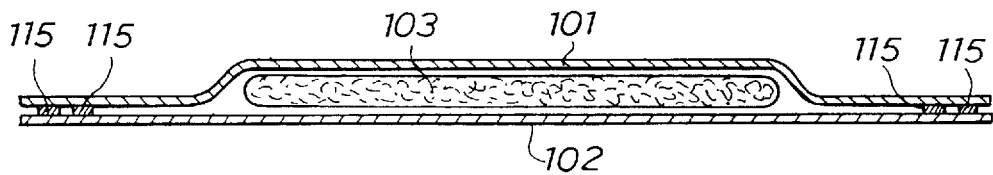
FIG. 16 is a cross-sectional view, taken on line 16—16 of FIG. 7, showing an outline of a sectional configuration of the shorts type disposable diaper according to one embodiment of the present invention.

The above-mentioned embodiments of the absorptive article of the present invention and the modes for carrying out the manufacturing methods thereof are based on the cross-sectional configuration (form) schematically shown in FIG. 16, taken on line 16—16 of FIG. 7 (FIG. 16 shows an example in which the first or second elastically expansible member 115a or 115b comprises two members). However, the shorts type disposable diaper of the present invention may take the configurations which will be described hereinafter and it can be manufactured in the manner as described hereinafter.

Figure 17:
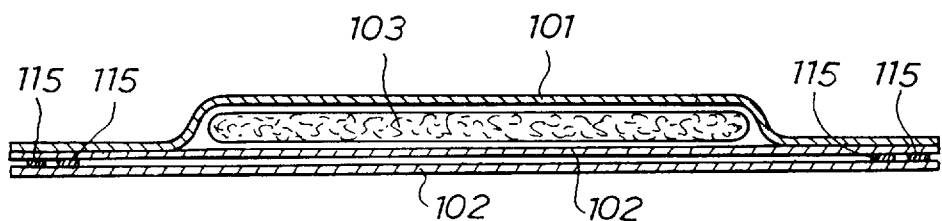
FIG. 17 is a view, like FIG. 16, showing an outline of a sectional configuration of a shorts type disposable diaper according to another embodiment of the present invention.

That is, the shorts type disposable diaper of the present invention may be constructed such that as shown in FIG. 17, the backsheet 102 comprises a laminated member having at least two layers, and the elastically expansible member 115 (first or second elastically expansible members 115a or 115b) is fixedly stretched in a predetermined position between the two layers of the laminated member and the absorber 103 is disposed on the laminated member. A film, a non-woven fabric, or the like may be used as the sheet constituting the laminated member. However, a sheet, which is used in a usual backsheet, should be provided at least on the outermost side.

In the case where a shorts type disposable diaper having a cross-sectional configuration as shown in FIG. 17 is manufactured, the manufacturing process for the absorptive body continuous member in the above-described mode may simply be changed as follows, for example.

That is, at least the first and second elastically expansible members 115 are fixedly stretched between adjacent layers of at least two layers of the continuous laminated member of a predetermined width constituting the backsheet 102 in such a manner as to sway in the width direction of the backsheet 102 at predetermined spaces, and thereafter, the continuous liquid permeable topsheet 102 of a predetermined width is provided on the absorber.

Figure 18:
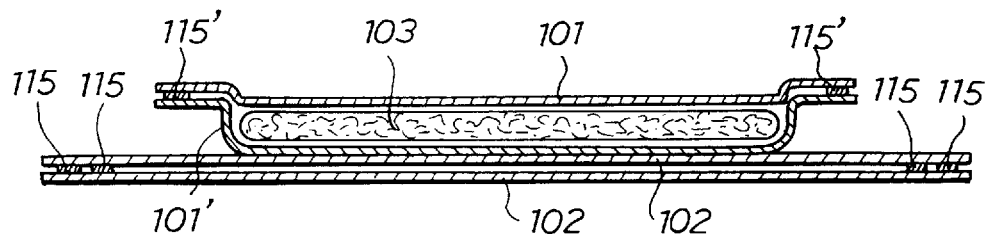
FIG. 18 is a view, like FIG. 16, showing an outline of a sectional configuration according to a further embodiment of a shorts type disposable diaper of the present invention.

Also, the shorts type disposable diaper of the present invention may be constructed such that as shown in FIG. 18, the absorber 103 beforehand interposed between the liquid permeable topsheet 101 and the liquid impermeable (or liquid permeable) sheet 101' is fixedly connected to the inner surface of the backsheet 102 which is comprised of the laminated member. In the Figure, reference numeral 115' denotes elastically expansible members disposed outwardly of the opposite side edges of the absorber 103.

In the case where the shorts type disposable diaper having a cross-sectional configuration as shown in FIG. 18 is manufactured, the above-mentioned manufacturing process for the absorptive body continuous member may simply be changed as follows, for example.

That is, at least the first and second elastically expansible members 115 are fixedly stretched between adjacent layers of at least two layers of the continuous laminated member of a predetermined width in such a manner as to sway in the width direction of the backsheet 102 at predetermined spaces, and thereafter, the absorber 103 beforehand interposed between the liquid permeable topsheet 101 and the liquid impermeable (or liquid permeable) sheet 101' is fixedly connected to the inner surface of the backsheet 102 which is comprised of the laminated member.

In the shorts type disposable diapers having the backsheet 102 comprised of a laminated member as shown in FIGS. 17 and 18, if the elastically expansible member 115 is disposed between the adjacent layers of the laminated member as illustrated in FIGS. 17 and 18, the contracting force of the elastically expansible member 115 does not prevail directly on the absorber 103 and therefore, the absorber 103 does not get out of shape and the contracting force of the elastically expansible member 115 is not disturbed, either.

Needless to say, the shorts type disposable diaper of the present invention is not limited to the above embodiments and modes for carrying out the manufacturing of the invention. For example, the elastically expansible members are not necessarily fixed at area over the entire length thereof as long as they are fixedly stretched at a predetermined part as a whole. Also, the sizes of the various parts, etc. may be properly set with reference to those of the illustrated embodiments or those of the component parts of the conventional shorts type disposable diaper. Although some description is omitted, the component members are appropriately fixedly connected together, either totally or partly, by adhesive or the like.

What is claimed is:

1. A shorts type disposable diaper including a waist opening portion, a pair of leg opening portions, and opposing side portions extending from the waist opening portion to the leg opening portions on opposing lateral sides of said diaper, said diaper comprising:

an absorptive body including a liquid permeable topsheet, a liquid impermeable backsheet, and an absorber interposed between said topsheet and said backsheet, said absorptive body being divided into a stomach side portion, an under-crotch portion, and a back side portion;

first and second non-overlapping elastically expansible members positioned to extend from the opposing side portions of said diaper around the first of two leg opening portions to the under-crotch portion, then laterally parallel and nonintersecting across substantially a center of the under-crotch portion of said diaper, and then around the second of two leg opening portions, wherein said first and second parallel elastically expansible members in said under-crotch portion are spaced apart from each other generally up to a distance of 20 mm; and a third continuous elastically expansible member disposed around an entirety of said diaper immediately adjacent the waist opening portion, whereby leakage of waste materials is substantially reduced while wearing comfortability is substantially increased.

2. The shorts type disposable diaper according to claim 1, wherein a thickness of said absorber at opposing longitudinal edges is less than a thickness of said absorber at a central area between said opposing longitudinal edges.

3. The shorts type disposable diaper according to claim 2, wherein said opposing longitudinal edges of said absorber are compressed relative to the central area thereof.

4. The shorts type disposable diaper according to claim 1, further comprising a layer of absorptive paper in combination with said absorptive body and extending in a lateral direction beyond the absorber such that opposing longitudinal edges of said absorber are formed of said absorptive paper.

5. The shorts type disposable diaper according to claim 1, wherein said first and second elastically expansible members each include a plurality of elastic strands.

6. The shorts type disposable diaper according to claim 5, wherein the plurality of elastic strands are spaced from 0.5 mm to 5.0 mm apart from an adjacent strand.

7. The shorts type disposable diaper according to claim 1, wherein each of said first and second elastically expansible members are unfixed in a portion of the under-crotch portion traversing said absorber.

8. The shorts type disposable diaper according to claim 1, wherein each of said first and second elastically expansible members have expanding stresses different from each other.

9. A shorts type disposable diaper including a waist opening portion, a pair of leg opening portions, and opposing side portions extending from the waist opening portion to the leg opening portions on opposing lateral sides of said diaper, said diaper comprising:

an absorptive body including a liquid permeable topsheet, a liquid impermeable backsheet, and an absorber interposed between said topsheet and said backsheet, said absorptive body being divided into a stomach side portion, an under-crotch portion, and a back side portion;

first and second elastically expansible members positioned at the pair of leg opening portions to extend from the opposing side portions of said diaper around the leg opening portions to the under-crotch portion, then laterally across substantially a center of the under-crotch portion of said diaper, the first and second elastically expansible members being nonintersecting and spaced apart from each other generally up to a distance of 20 mm, or having a single common overlapping region in the under-crotch portion defined by superimposing the first and second elastically expansible members laterally and across substantially the center of the under-crotch portion of said diaper, said overlapping region including said first and second elastically expansible members lying upon each other in a substantially parallel manner; and a third continuous elastically expansible member disposed around an entirety of said diaper immediately adjacent the waist opening portion, whereby leakage of waste materials is substantially reduced while wearing comfortability is substantially increased.

10. The shorts type disposable diaper according to claim 9, wherein a thickness of said absorber at opposing longitudinal edges is less than a thickness of said absorber at a central area between said opposing longitudinal edges.

11. The shorts type disposable diaper according to claim 9, wherein said opposing longitudinal edges of said absorber are compressed relative to the central area thereof.

12. The shorts type disposable diaper according to claim 9, further comprising a layer of absorptive paper in combination with said absorptive body and extending in a lateral direction beyond the absorber such that opposing longitudinal edges of said absorber are formed of said absorptive paper.

13. The shorts type disposable diaper according to claim 9, wherein said first and second elastically expansible members each include a plurality of elastic strands.

14. The shorts type disposable diaper according to claim 13, wherein the plurality of elastic strands are spaced from 0.5 mm to 5.0 mm apart from an adjacent strand.

15. The shorts type disposable diaper according to claim 9, wherein each of said first and second elastically expansible members are unfixed in a portion of the under-crotch portion traversing said absorber.

16. The shorts type disposable diaper according to claim 9, wherein each of said first and second elastically expansible members have expanding stresses different from each other.

* * * * *